United States Patent [19]
McGill et al.

[11] Patent Number: 5,891,421
[45] Date of Patent: Apr. 6, 1999

[54] PRECIPITATED SILICAS HAVING IMPROVED DENTIFRICE PERFORMANCE CHARACTERISTICS AND METHODS OF PREPARATION

[75] Inventors: Patrick D. McGill, Darlington; Satish K. Wason, Bel Air, both of Md.

[73] Assignee: J.M. Huber Corporation, Edison, N.J.

[21] Appl. No.: 621,288

[22] Filed: Mar. 22, 1996

[51] Int. Cl.$^6$ .............................. A61K 7/16; C01B 33/12
[52] U.S. Cl. ..................... 424/49; 433/228.1; 423/339
[58] Field of Search ................ 423/339; 433/228.1; 424/49

[56] References Cited

U.S. PATENT DOCUMENTS

| | | | |
|---|---|---|---|
| 3,792,531 | 2/1974 | Rossi | 433/228 |
| 3,928,540 | 12/1975 | Morgan | 423/339 |
| 4,038,098 | 7/1977 | Wason | 106/288 B |
| 4,217,264 | 8/1980 | Mabie et al. | 433/228.1 |
| 4,427,799 | 1/1984 | Orlowski et al. | 433/228.1 |
| 4,581,217 | 4/1986 | Shinpo | 423/339 |
| 4,590,052 | 5/1986 | Chevallier et al. | 423/335 |
| 4,906,446 | 3/1990 | Engelbrecht et al. | 423/335 |
| 5,030,286 | 7/1991 | Crawford et al. | 106/435 |
| 5,034,207 | 7/1991 | Kerner et al. | 423/339 |
| 5,496,387 | 3/1996 | Culler | 51/295 |

FOREIGN PATENT DOCUMENTS

| | | |
|---|---|---|
| 0308165 | 3/1989 | European Pat. Off. . |
| 0 535 943 A1 | 4/1993 | European Pat. Off. . |
| 1135432 | 8/1962 | Germany . |
| 2406672 | 8/1974 | Germany . |
| 63-139045 | 6/1988 | Japan . |
| 49039757 | 10/1994 | Japan . |
| WO 92/02454 | 2/1992 | WIPO . |

*Primary Examiner*—Peter F. Kulkosky

[57] ABSTRACT

Precipitated silica compositions, and methods for making the same, with improved dentifrice performance characteristics. In particular, precipitated silica compositions of the present invention have a 40% slurry viscosity build of less than approximately 20,000 centipoise and a 10% Brass Einlehner abrasion value of approximately 2.5 to 20.0 mg loss/100,000 rev. Precipitated silica compositions of the present invention also have reactor slurry average particle sizes (50%) of approximately 10 to 50 μm. Methods for preparing precipitated silicas of the present invention include the steps of: (a) adding sodium silicate and a mineral acid to a reactor, thereby initiating a precipitation reaction between the reactor contents; and (b) subjecting the reactor contents to shearing forces as the reaction proceeds.

15 Claims, 1 Drawing Sheet

PRECIPITATED SILICAS HAVING IMPROVED DENTIFRICE PERFORMANCE CHARACTERISTICS AND METHODS OF PREPARATION

BACKGROUND OF THE INVENTION

1. Field of the Invention

This invention relates to improved precipitated silica compositions. More particularly, the present invention relates to improved precipitated silica compositions that impart improved cleaning and abrasive performance to dentifrice formulations. Further, the present invention relates to methods for preparation of the improved precipitated silica compositions of this invention.

2. Description of the Related Art

The function of an abrasive substance in formulations intended for use in dentifrice compositions is to remove various deposits including pellicle film from the surface of teeth. Pellicle film is tightly adherent and often contains brown or yellow pigments which impart an unsightly appearance to the teeth. While cleaning is important, however, the abrasive should not be so abrasive as to damage the teeth. Thus, an effective dentifrice abrasive material should maximize film removal without causing undue abrasion to the hard tooth tissue. Accordingly, dental researchers are continually seeking dentifrice abrasives that demonstrate satisfactory levels of cleaning without being unduly abrasive and damaging to oral tissues.

Precipitated silica (silicon dioxide) abrasive compositions and their use in dentifrice formulations are well known. In known silicas, however, there is a nearly linear relation relationship between abrasiveness and cleaning ability. As a result, the ability to develop dentifrice compositions with improved cleaning ability is limited by the tendency of the silicas to become more abrasive as their cleaning properties improve. Thus, there is a need for silicas for use in dentifrice compositions that impart improved cleaning ability to the toothpaste compositions without being overly abrasive and, therefore, damaging to oral tissues.

The cleaning and abrasiveness properties of dentifrice compositions are typically expressed in terms of Pellicle Cleaning Ratios ("PCR") and Radioactive Dentin Abrasion ("RDA") values, respectively. The PCR test measures the ability of a dentifrice composition to remove pellicle film from a tooth under fixed brushing conditions. The PCR test is described generally in "*In Vitro Removal of Stain With Dentifrice*", G. K. Stookey, T. A. Burkhard and B. R. Schemehorn, J. Dental Research, 61, 1236–9, 1982, which is incorporated herein by reference. The RDA test measures the abrasiveness of dentifrice compositions by measuring the amount of radio-labeled dentin removed from a tooth under fixed brushing conditions. Both PCR and RDA results vary depending upon the nature and concentration of the components of the dentifrice composition.

One key variable affecting PCR and RDA results is the nature and quantity of silica abrasive loaded into the dentifrice composition. It is generally believed that higher concentrations of a given silica abrasive will increase PCR results. Thus, it is desirable to load silica abrasives into dentifrice compositions at relatively high concentrations to improve cleaning. It is also generally believed that relatively hard or abrasive silicas tend to impart relatively high (poor) RDA values to dentifrice compositions. Thus, it is desirable to provide relatively soft or low abrasiveness silicas for use in making dentifrice compositions with low RDA values without sacrificing cleaning properties.

Unfortunately, however, known silicas tend to build viscosity relatively rapidly in dentifrice compositions. As a result most commercial dentifrice compositions contain only approximately 15 to 25% by weight of silica abrasive. Higher loading levels of known silicas tend to make the dentifrice compositions too viscous for their intended purpose. Thus, there is a need for silicas with lower viscosity build characteristics that can be loaded into dentifrice compositions at greater concentrations.

Also, known silicas tend to have a relatively large reactor slurry average particle size (APS). APS is believed to be correlated to abrasivity. While it is possible to dry and mill a silica to almost any desired final, or milled APS, the milling process is itself time consuming and expensive and can have undesired side effects, such as causing discoloration of the silica. More importantly, it is now believed that silicas with lower reactor slurry APS are softer than similar silicas with higher reactor slurry APS. As a result, it is now believed that if two silicas are milled to the same dry milled APS, the silica with the smaller reactor slurry APS will be softer than the silica with the higher reactor slurry APS, will have a lower functional APS and will, therefore, be less abrasive. Accordingly, there is a need for silicas with smaller reactor slurry APS.

It is accordingly an object of the present invention to provide novel precipitated silica compositions that impart improved performance in dentifrice formulations.

It is a further object of the present invention is to provide precipitated silica compositions that impart improved cleaning and abrasive characteristics to dentifrice formulations.

It is a further object of the present invention to provide precipitated silica compositions that have relatively low viscosity build characteristics compared to known silicas.

It is a further object of the present invention to provide precipitated silica compositions that have relatively low reactor slurry APS compared to known silicas.

It is a further object of the present invention is to provide methods for the preparation of the novel precipitated silica compositions of the invention by acidulation of an alkali metal silicate by a mineral acid in the absence or presence of an electrolyte.

Further objects and advantages of the present invention will become apparent from the detailed description of the preferred embodiments which follows.

SUMMARY OF THE INVENTION

A precipitated silica composition, wherein the silica has: a 40% slurry viscosity build of less than approximately 20,000 centipoise; and a 10% Brass Einlehner abrasion value of approximately 2.5 to 8.0 mg loss/100,000 rev.

A precipitated silica composition, wherein the silica has a reactor slurry average particle size (median value or "50%") of approximately 10 to 50 µm.

A method for preparing precipitated silicas comprising the steps of: (a) adding sodium silicate and a mineral acid to a reactor, thereby initiating a precipitation reaction between the reactor contents; and (b) subjecting the reactor contents to shearing forces as the reaction proceeds.

DESCRIPTION OF THE PREFERRED EMBODIMENT(S)

Figure 1:
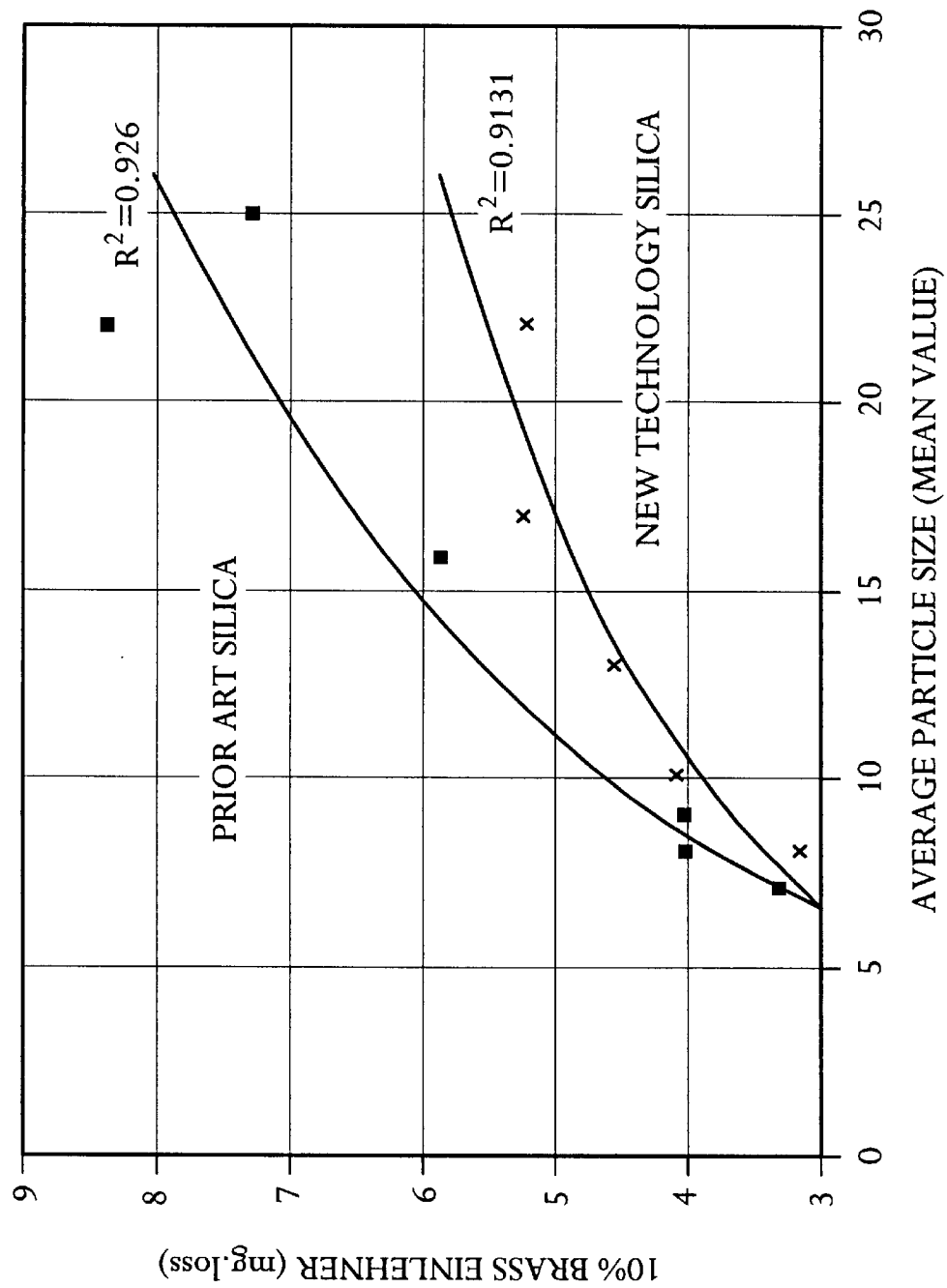
FIG. 1 is a graphic depiction of the relationship between 10% Brass Einlehner and reactor slurry average particle size for prior art silica and silica in accordance with the invention.

The present invention provides novel amorphous precipitated silica compositions which are useful to impart improved cleaning and abrasive characteristics to dentifrice formulations. The silicas of the present invention are preferably characterized as synthetic hydrated amorphous silicas, also known as silicon dioxides or $SiO_2$. In particular, the silicas of the present invention have smaller reactor slurry average particle sizes (APS) than known silicas. Silicas of the present invention also have a significantly lower viscosity build than known silicas of comparable abrasiveness. Accordingly, silicas of the present invention may be loaded into dentifrice compositions in greater concentrations than known silicas, resulting in dentifrice compositions with improved cleaning properties and without undue abrasiveness.

Reactor slurry APS is defined as the APS of the precipitated silica compositions as measured after processing in the reactor or washed slurry but before drying, milling, and/or use. Reactor slurry APS is measured using a Microtrac II Particle Analyzer manufactured by Leeds and Northrup. Silicas of the present invention preferably have a reactor slurry APS of approximately 10 to 50 μm, and more preferably approximately 10 to 20 μm. All reactor slurry APS values provided herein are median values ("50%") unless otherwise indicated.

Without limiting itself to any particular theory, Applicant believes that the relatively low reactor slurry APS results in the preparation of silicas with relatively low average functional particle size, where functional particle size is defined as the particle size of the silica while it is in use (e.g., during the brushing process). In other words, Applicant believes that the silicas of the present invention are softer than silicas with higher reactor slurry APS. As a result, Applicant believes that, in use, the silicas of the present invention (i.e., with relatively low reactor slurry APS) break up into smaller and, therefore, less abrasive particles more readily than silicas with higher reactor slurry APS. The silicas of the present invention are, therefore, less abrasive than known silicas with the same milled APS. In addition, silicas of the present invention have improved milling properties because they are initially smaller and require less milling, and because they are softer and, therefore, tend to break up into smaller particles more readily. As a result, silicas of the present invention are less likely to suffer from the graying caused by excessive milling.

Silicas according to the present invention are also relatively less abrasive than known silicas of approximately the same milled APS and viscosity build. Several tests are used to measure abrasiveness of silicas. The most direct measure is the Brass Einlehner Abrasion test. In the Brass Einlehner Abrasion test, an Einlehner AT-1000 Abrader is used as follows: (1) a Fourdrinier brass wire screen is weighed and exposed to the action of a 10% aqueous silica suspension for a fixed length of time; (2) the amount of abrasion is then determined as milligrams brass lost from the Fourdrinier wire screen per 100,000 revolutions. 10% Brass Einlehner (10% BE) results are expressed in milligrams loss/100,000 revolutions. Silicas in accordance with the present invention have 10% BE values of approximately 2.5 to 20.0 mg loss/100,000 revolutions, and more preferably approximately 2.5 to 8.0 mg loss/100,000 revolutions, and most preferably approximately 3 to 6 mg loss/100,000 revolutions.

Silicas in accordance with the present invention also tend to have a relatively small impact on viscosity of dentifrice compositions compared to known silicas. The tendency of a silica to increase the viscosity of a fluid is referred to as "viscosity build." Viscosity may be measured by a viscosimeter and may be expressed in centipoise. In a 40% slurry test, silicas in accordance with the present invention, having a moisture content of 5 to 7% and where moisture is measured by weight loss at 105° C. for 2 hours, have a viscosity of less than approximately 20,000 centipoise, and preferably less than approximately 12,000 centipoise, and most preferably less than 7,000 centiposies. Detailed procedures for the 40% slurry test are set forth in the Examples.

Silicas in accordance with the present invention are preferably Low Structure silicas in accordance with the definitions set forth in the J. Soc.Cosmet. Chem. 29, 497–521 (August, 1978), and Pigment Handbook: Volume 1, Properties and Economics, Second Edition, Edited by Peter A. Lewis, John Wiley & Sons, Inc. , 1988, p. 139–159.

Silicas in accordance with the present invention preferably have an oil absorption in the range of approximately 60 to 120 cc/100 g and more preferably approximately 80 to 100 cc/100 g, and most preferably approximately 80 to 90 cc/100 g. In the present specification oil absorption is measured using the ASTM rub-out method D281.

Silicas in accordance with the present invention preferably have a BET surface area in the range of approximately 50 to 250 $m^2$/g. Surface area is determined by the BET nitrogen adsorption method of Brunaur et al, *J. Am. Chem. Soc.*, 60, 309 (1938).

Silicas in accordance with the present invention also preferably exhibit fluoride availability and compatibility values in the range of approximately 90–100%, as defined in U.S. Pat. No. 4,340,583, which is incorporated by reference herein.

Silicas in accordance with the present invention preferably have mercury intrusion void volume values in the range of 1.0 to 4.0 cc/g and more preferably 1.2 to 2.0 cc/g. The pore volumes (mercury pore volume) are determined using an Autopore II 9220 Porosimeter (Micromeritics Corporation). This instrument measures the void volume and pore size distribution of various materials. Mercury is forced into the voids as a function of pressure and the volume of mercury intruded per gram of sample is calculated at each pressure setting. Total pore volume expressed herein represents the cumulative volume of mercury intruded at pressures from vacuum to 60,000 psi. Increments in volume (cc/g) at each pressure setting are plotted against the pore radius corresponding to the pressure setting increments. The peak in the intruded volume versus pore radius curve corresponds to the mode in the pore size distribution and identifies the most common pore size in the sample.

Silicas in accordance with the present invention preferably have a pH of approximately 4.0 to 8.5 and more preferably from 6.5 to 8.5, as measured in a 5% aqueous slurry.

Silicas in accordance with the present invention preferably have a Pellicle Cleaning Ratio (PCR) of approximately 70 to 140 and preferably approximately 100 to 130.

Silicas in accordance with the present invention preferably have a pour density of approximately 15–25 lb./$ft^3$ and a pack density of approximately 25–35 lb./$ft^3$. Bulk density is measured by measuring the volume in liters occupied by a given weight of the silica, and is reported in pounds per cubic foot.

Silicas in accordance with the present invention preferably have a brightness value of approximately 90 to 100. To measure brightness, fine powder materials are pressed into a smooth surfaced pellet and are evaluated using a Technidyne Brightimeter S-5/BC. The Technidyne Brightimeter S-5/BC has a dual beam optical system where the sample is illuminated at an angle of 45°, and the reflected light viewed at 0°.

This method conforms to TAPPI test methods T452 and T646, and ASTM Standard D985.

The precipitated silicas of the present invention may be prepared by a fresh water, or electrolyte solution, acidulation process wherein silica (silicon dioxide or $SiO_2$) is precipitated by reaction of an alkali metal silicate and a mineral acid in aqueous solution. The alkali metal silicate may be any alkali metal silicate, but sodium silicate is preferred. While any mineral acid may be used in the process, sulfuric acid is a preferred reactant. In the preferred fresh water process, no electrolyte such as alum, $Na_2SO_4$, or NaCl, is present during the reaction.

In the preferred process, an aqueous sodium silicate solution is provided wherein the sodium silicate is present in a concentration of approximately 8.0 to 35 weight percent, preferably 8.0 to 15 weight percent. The $Na_2O:SiO_2$ ratio in the silicate solution should range from about 1 to 3.5 and preferably from about 2.5 to 3.4. The sulfuric acid reactant will preferably have a concentration of about 6 to 35% in water, more preferably about 9.0 to 15 weight percent.

Silicas in accordance with the present invention are prepared as follows:

1. A portion of the sodium silicate solution is charged to a reactor comprising a reaction chamber and a means for subjecting the reactor contents to shearing forces. In the preferred embodiment, about 5 to 15% of the total stoichiometric amount of sodium silicate solution, preferably about 8 to 12%, should be placed in the reactor to serve as initiating nuclei for the silica. In a preferred embodiment, the shear means is a line blender, such as the Lightnin Mixer model 5-LBC-500 (5 hp, 1750 rpm) or model 1-LBDS-75 (¾ hp, 1750 rpm), a recirculation pump, such as the Labour DZT 30 (25 hp, 1750 rpm), a high shear reactor agitator blade, steam sparging apparatus, air sparging apparatus, a steam jacket, bead milling, or a combination thereof.

2. The aqueous solution of sodium silicate in the reactor is then preheated to a temperature in the range of about 160° to 210° F., preferably about 185° to 195° F. Prior to introduction into the reactor, the remaining sodium silicate solution is preferably preheated to approximately 150° to 185° F., and the acid solution is preferably preheated to approximately 90° to 95° F.

3. Once the reactor solution and the remaining reactants have reached the desired temperatures, the remaining reactants are added simultaneously to the reactor. The sodium silicate solution and sulfuric acid are metered into the sodium silicate solution in the reactor over an addition time of about 40 to 60 minutes, but preferably over approximately 50 minutes. Rates of addition of the reactants depend upon the Mol. ratio and concentration of the silica and the concentration of the acid. Generally, 1 Mol. sodium is neutralized with one Mol. sulphuric acid. Thus, the ratio of sodium silicate addition rate to acid addition rate are as follows given the reactants set forth below:

| Sodium Silicate Mol. ratio and conc. | Acid | Sodium Silicate Rate/Acid Rate |
|---|---|---|
| 1 Mol. ratio, 35% conc. | 6% | 0.192 |
| 3.5 Mol. ratio, 8% conc. | 35% | 17.4 |
| 2.5 Mol. ratio, 15% conc. | 9% | 1.47 |
| 3.4 Mol. ratio, 8% conc. | 15% | 6.4 |
| 2.65 Mol. ratio, 13.3% conc. | 11.4% | 2.24 |

4. At the end of this addition time, the silica has precipitated and the sodium silicate addition is terminated. Addition of the acid may be continued until the reactor slurry reaches the desired pH. The preferred slurry pH is approximately 5.4 to 6.4, and is more preferably approximately 5.5 to 5.7. At this stage, the silica has precipitated to provide a mixture of the precipitated silica and the reaction liquor.

5. Once the desired final slurry pH is reached, digestion begins and the reaction temperature is raised to approximately 190° to 210° F. and preferably to approximately 199° F.±4° F. Digestion at elevated temperature is continued for approximately 5 to 60 minutes, and preferably for approximately 10 minutes.

6. Sometime prior to drying, the reaction products are subjected to shearing forces. In a preferred embodiment, the contents of the reactor are subjected to shearing forces during the reaction and digestion steps. In a preferred embodiment of the present invention, shear is applied to the contents of the reactor from the time the initial silicate reaches the desired reaction temperature until the digestion is complete. Alternatively, shear may be applied to the reactor contents for only a portion of the reaction time. In an alternative preferred embodiment of the present invention, shear is applied to the contents of the reactor beginning approximately 30 minutes after the reactants are first added to the initial nuclei and continued for approximately 45 minutes until digestion is complete. The amount of shear can be expressed in terms of the number of times the entire reactor contents are recirculated during the reaction time. The minimum shear rate should be 0.75. Preferably the shear rate is greater than 2.68 (e.g., 450 g.p.m. for 45 min. in 7,545 gal reactor). Most preferably, the shear rate is approximately 4.5 (e.g., 450 g.p.m. for 75 min. in a 7,545 gal. reactor). Alternatively, the reaction product may be subjected to shearing forces after the reaction is complete, but prior to drying.

7. After the digestion is complete, the pH may again be adjusted. In a preferred embodiment, the pH is adjusted to about 5.6.

8. The reaction mixture may then be filtered and washed with water to remove salts from the filter cake.

9. The filter cake may then be dried, preferably by conventional spray drying to produce a precipitated silica containing about 3 to 10% moisture.

10. The precipitated silica may then be milled to the desired particle size.

EXAMPLES

The following examples are presented to illustrate the invention, but the invention is not to be considered as limited thereto. In the following examples, parts are by weight unless otherwise indicated.

Example 1

434 gal. of sodium silicate solution (3.73 percent $Na_2O$, 9.57 percent $SiO_2$) of specific gravity 1.12 was added into a 7,545 gallons stainless steel reactor jacketed for steam heating. The reactor was provided with a Labour DZT30 450 g.p.m. pump and a 5-LBC-500 Lightnin Mixer line blender. The reaction medium was preheated to 195°±5° F. The remaining silicate was heated to approximately 185°±5° F. and the acid was heated to approximately 92° F. After the initial nuclei silicate temperature reached 195°±5° F., the pump and line blender were turned on. Thereafter, sulfuric acid, 11.4% concentration (specific gravity 1.079), and the remainder of the stoichiometric amount of the sodium silicate solution were separately simultaneously metered into the reaction medium at the rate of 41.3°±0.5 g.p.m. acid and 92.7°±0.5 g.p.m. sodium silicate while maintaining the reaction temperature at 195°±5° F. The silicate addition was discontinued after 48 minutes. The acid addition was thereafter continued until the slurry pH was between 5.8 to 6.0. The reaction slurry was then digested for 10 minutes at 199°±4° F. The reaction pH was adjusted again to between 5.5 to 5.7. Shearing of the reactor slurry was then stopped. The resulting silica slurry was filtered and washed to remove most of the reaction by-product (sodium sulfate). The filter cake was dried and the dry product milled to a milled APS of approximately 10 μm (50%).

Example 2

The basic procedure of Example 1 was repeated with only those variations set forth in Table 1.

Example 3

The basic procedure of Example 1 was repeated without applying shear to the reactor contents and with only those variations set forth in Table 1.

The dry silicas of examples 1–3 were subjected to various tests, the results of which are set forth in Table 1. The procedures for the tests are set forth above and/or are generally known to one of ordinary skill in the art.

TABLE 1

|  | Example 1 | Example 2 | Example 3 |
|---|---|---|---|
| % initial silicate | 8–10 | 8–10 | 8–10 |
| reaction temp (°F.) | 195 ± 5 | 195–197 | 190 ± 5 |
| batch pH | 5.5–5.7 | 5.8–6.0 | 5.8–6.0 |
| line blender capacity (g.p.m.) | 450 | 450 | 0 |
| line blender time (min) | 75 | 45 | 0 |
| acid add. rate (g.p.m.) | 41.3 | 41.3 | 41.5 |
| sodium silicate add. rate (g.p.m.) | 92.7 | 92.7 | 92.7 |
| reaction time (min) | 64 | 64 | 65 |
| cure time (min) | 10 | 10 | 10 |
| reactor slurry APS(MV) (μm) | 45.7 | 78.08 | 82.7 |
| reactor slurry APS(50%) (μm) | 18.5 | 46.2 | 43.1 |
| milled APS(MV) (μm) | 10.49 | 12.7 | 14.5 |
| 10% Brass Einlehner (mg loss/100,000 rev.) | 4.32 | 5.47 | 3.97 |
| 40% slurry viscosity (centipoise) | 6,520 | 6,940 | 31,000 |
| oil absorption (cc/100 g) | 86 | 89 | 87 |
| brightness | 98.5 | 98.4 | 98.2 |
| BET surface area (m²/g) | 150 | 71 | 71 |
| pour density (lb./ft³) | 17.8 | 16.87 | 15.23 |
| pack density (lb./ft³) | 31.2 | 28.3 | 28.39 |
| mercury intrusion (cc/g) | 1.573 | 1.87 | 1.88 |

Example 4

Silica prepared in accordance with the procedures of Example 1 were milled to varying particle sizes and tested for abrasiveness as shown in Table 2.

TABLE 2

| Sample | APS (MV) (μm) | 10% Brass Einlehner (mg loss/100,000 rev.) |
|---|---|---|
| 1A | 8.46 | 3.17 |
| 1B | 10.19 | 4.09 |

TABLE 2-continued

| Sample | APS (MV) (μm) | 10% Brass Einlehner (mg loss/100,000 rev.) |
|---|---|---|
| 1C | 13.28 | 4.55 |
| 1D | 17.07 | 5.24 |
| 1E | 22.48 | 5.24 |

Example 5

Silica prepared in accordance with the procedures of Example 3 were milled to varying particle sizes and tested for abrasiveness as shown in Table 3.

TABLE 3

| Sample | APS (MV) | 10% Brass Einlehner (mg loss/100,000 rev.) |
|---|---|---|
| 3A | 6.60 | 3.34 |
| 3B | 8.37 | 4.03 |
| 3C | 9.45 | 4.03 |
| 3D | 16.72 | 5.87 |
| 3E | 22.02 | 8.4 |
| 3F | 25.32 | 7.31 |

The results of Examples 4 and 5 are shown in FIG. 1. As shown in FIG. 1, for a given dry, milled APS (MV), silicas prepared in accordance with the present invention, i.e., prepared by applying shear to the silica prior to drying and milling, are less abrasive than silicas prepared without shear.

In the preceeding examples, the 40% slurry test was conducted as follows:

A. Using a tachometer, mark setting on rheostat that provides 300 rpm to mixing shaft. Repeat for 600 rpm.

B. In a large weighing pan, weigh out 340.0°±0.05 g of silica.

C. Tare a 4000 ml metal beaker, and add 510.0°±0.05 g of deionized water.

D. Position mixing blade and shaft in center of metal beaker so that blade is close to bottom of beaker, but does not touch.

E. Start mixer at 300 rpm. Add silica over a 2–3 minute period.

F. Scrape sides of beaker to thoroughly mix all silica in the beaker.

G. Increase rpm to 600, and time mixing for 5 minutes. Periodically scrape sides of beaker and mixing blade.

H. At 5 minutes, stop mixing and transfer slurry into 800 ml plastic beaker.

I. Set Brookfield viscometer (model ½ RVDV-II+) at 5 rpm.

J. Fit the Brookfield viscometer with the appropriate spindle. The T-B spindle may be used with moderate viscosities, but it will become necessary with higher viscosities to select a spindle that will produce a mid-scale reading. Lower spindle so that it is barely covered by slurry, and is centered in the beaker.

K. Turn on viscometer and helipath stand. Record measurement after 2 complete revolutions. Using a Brookfield chart, convert scale reading into centipoise.

Note: Mixing speeds may need to be altered slightly for slurries of very high viscosity. It is important to impart as little shear as possible to the slurry, therefore, use of the least amount of mixing speed necessary to produce a homogeneous slurry is suggested.

In the preceeding examples, the Brass Einlehner abrasion test was conducted as follows:

A. Equipment: Einlehner AT-1000; Wire Screen for Einlehner (Phosphor Bronze P.M. wire disc); 10 PVC tubing from Einlehner; Top loading balance (minimum 2000 g, weighing to 0.1 g); Analytical balance (weighing to 0.01 mg); drying oven (convection type); 2 liter metal beaker; mixer equipped with propeller type agitator and rheostat; tweezers; lint free toweling; liquid dishwasher detergent.

B. Preparation of wire screens, PVC tubing and backing plates: New screens, PVC tubing, and backing plates may have residual oil left from their manufacture which must be removed as follows: (1) prepare solution of liquid soap and hot tap water; (2) soak screens, tubing, and plates for ½ hour in soap solution; (3) manually wash screens, tubing, and plates (do not use any utensil that may abrade the screens); (4) rinse thoroughly with hot water; (5) place in convection drying oven for 15–20 minutes at 60° C.; (6) remove from oven and cool on lint-free surface.

C. Einlehner Preparation: (1) on analytical balance weighing to 0.01 mg, weigh screen; (2) prepare test cylinder by seating rough edge of wearing plate into male thread portion of testing cylinder; (3) invert Einlehner cylinder and seat the clamping ring onto the base of the cylinder; (4) place screen on top of clamping ring, with smooth side against the ring; (5) invert the bottom section of cylinder containing wearing plate onto top portion with clamping ring and screen, then assemble; (6) place one piece of PVC tubing onto each end of barrel (testing body), notches on the PVC tubing face inward and are placed on the barrel so that the notches line up with the number 4; (7) barrel is placed onto carrier clamps so that flat sides of barrel are held loosely by carrier clamps.

D. Test Procedures: (1) weigh 900±0.05 g of deionized water into a 2 liter metal beaker; (2) into same beaker, add 100±0.05 g of homogenous silica sample; (3) mix sample for 5 min., set rheostat to produce a moderate vortex around agitator; (4) remove sample and without allowing sample to settle, place in Einlehner cylinder; (5) place cylinder onto Einlehner base, seat teeth at top of agitator shaft into their slots; (6) turn on power switch and set program selector for 87,000 rotations, push start button; (7) after test cycle has been completed, remove test cylinder from Einlehner apparatus; (8) discard excess sample and disassemble test cylinder; (9) wash cylinder with hot tap water; (10) flush screen under hot running water and rub briskly to remove excess sample from screen; (11) place screen in 60° C. convection oven and dry for 20–25 min., remove screen and wrap in lint-free towel, return to oven for additional 5 min. to drive moisture from towel; (12) remove from oven and place in desiccator, cool to ambient temperature, about 10 min.; (13) weigh screen on analytical balance.

It will be understood that various changes in the details, materials, and arrangements of the parts which have been described and illustrated in order to explain the nature of this invention may be made by those skilled in the art without departing from the principle and scope of the invention as expressed in the following claims.

What is claimed is:

1. An amorphous precipitated silica of low structure for use in dentifrice formulations, said silica comprising:

a BET surface area of approximately 50 to 250 $m^2/g$;

an oil absorption of approximately 60 to 120 cc/100 g;

a mercury intrusion void volume of 1.0 to 4.0 cc/g;

a 5% aqueous slurry pH of approximately 4.0 to 8.5;

a reactor slurry average particle size, in terms of median value, of approximately 10 to 50 $\mu$m;

a 40% slurry viscosity build of less than approximately 20,000 centipoise; and a 10% Brass Einlehner abrasion value of approximately 2.5 to 20.0 mg loss/100,000 rev;

wherein said silica is less abrasive than a silica having substantially equivalent physical properties prepared without shearing and having a reactor slurry average particle size greater than approximately 10 to 50 $\mu$m.

2. The precipitated silica of claim 1, wherein the 10% Brass Einlehner abrasion value is approximately 2.5 to 8.0 mg loss/100,000 rev.

3. The precipitated silica of claim 1, wherein the 10% Brass Einlehner abrasion value is approximately 3.0 to 6.0 mg loss/100,000 rev.

4. The precipitated silica of claim 1, wherein the 40% slurry viscosity build is less than approximately 12,000 centipoise.

5. The precipitated silica of claim 1, wherein the 40% slurry viscosity build is less than approximately 7,000 centipoise.

6. A method for preparing an amorphous precipitated silica of low structure for use in dentifrice formulations according to claim 1, comprising the steps of:

a. adding sodium silicate and a mineral acid to a reactor, thereby initiating a precipitation reaction between the reactor contents to yield a reaction product; and b. subjecting said reaction product to shearing forces prior to drying said reaction product.

7. The method of claim 6, wherein said reaction product is subjected to shearing forces during said precipitation reaction.

8. The method of claim 7, wherein said shearing forces are induced by a line blender.

9. The method of claim 7, wherein said shearing forces are induced by a recirculation pump.

10. The method of claim 9, wherein said recirculation pump operates at a rate sufficient to turn the reactor contents over at least 0.75 times during the reaction.

11. The method of claim 9, wherein said recirculation pump operates at a rate sufficient to turn the reactor contents over at least 2.68 times during the reaction.

12. The method of claim 9, wherein said recirculation pump operates at a rate sufficient to turn the reactor contents over at least 4.5 times during the reaction.

13. The method of claim 7, wherein the reactor contents are subjected to shearing forces throughout said precipitation reaction.

14. An amorphous precipitated silica of low structure for use in dentifrice compositions prepared in accordance with claim 6, 7, 8, 9, 10, 11, 12, or 13.

15. The method of claim 6, wherein said reaction product has, in terms of median value a reactor slurry average particle size of approximately 10 to 20 $\mu$m.

* * * * *